United States Patent [19]
Briscoe

[11] Patent Number: 5,807,328
[45] Date of Patent: Sep. 15, 1998

[54] BALLOON CATHETER ASSEMBLY WITH SELECTIVELY OCCLUDED AND VENTED LUMEN

[75] Inventor: Roderick E. Briscoe, Rockford, Mich.

[73] Assignee: Medtronic, Inc., Minneapolis, Minn.

[21] Appl. No.: 625,911

[22] Filed: Apr. 1, 1996

[51] Int. Cl.[6] .................................................. A61M 29/00
[52] U.S. Cl. ........................ 604/96; 604/102; 604/158; 604/164; 604/169; 606/194
[58] Field of Search .................. 604/96, 97, 99, 604/102, 158, 164, 165, 167, 169, 246, 247, 249, 250, 256; 606/191, 194

[56] References Cited

U.S. PATENT DOCUMENTS

| | | |
|---|---|---|
| 4,327,722 | 5/1982 | Groshong et al. ...................... 604/169 |
| 4,535,757 | 8/1985 | Webster, Jr. . |
| 4,598,707 | 7/1986 | Agdanowski et al. .................... 604/99 |
| 4,689,041 | 8/1987 | Corday et al. . |
| 4,850,969 | 7/1989 | Jackson .................... 604/102 |
| 4,917,667 | 4/1990 | Jackson . |
| 5,021,045 | 6/1991 | Buckberg et al. . |
| 5,033,998 | 7/1991 | Corday et al. . |
| 5,041,084 | 8/1991 | DeVries et al. ......................... 604/169 |
| 5,078,681 | 1/1992 | Kawashima ................................ 604/99 |
| 5,197,952 | 3/1993 | Marcadis et al. . |
| 5,324,260 | 6/1994 | O'Neill et al. . |
| 5,385,548 | 1/1995 | Williams et al. . |
| 5,505,698 | 4/1996 | Booth et al. .............................. 604/96 |

Primary Examiner—Wynn Wood Coggins
Assistant Examiner—Bhisma Mehta
Attorney, Agent, or Firm—Foley & Lardner

[57] ABSTRACT

A catheter assembly having a selectively occluded and vented lumen is provided. The catheter includes an obturator for preventing the back flow of fluid from the distal tip of the catheter into a balloon provided on the body of the catheter. The catheter has at least one groove for venting the balloon during the process of inserting the catheter assembly into fluid under pressure. The combination of the obturator and the venting groove prohibits premature inflation of the balloon by pressurized fluid entering the distal end of the catheter and also enables for the venting of any air entrapped inside the balloon prior to inflation thereof. When incorporated into a retrograde cardioplegia solution catheter, this structure dramatically reduces the force needed to insert the catheter assembly into the coronary sinus and also reduces trauma to the tissue of the coronary sinus during the insertion process.

26 Claims, 6 Drawing Sheets

BALLOON CATHETER ASSEMBLY WITH SELECTIVELY OCCLUDED AND VENTED LUMEN

BACKGROUND OF THE INVENTION

1. Field of the Invention

This invention relates to catheter assemblies and, more particularly, to balloon catheter assemblies in which the lumen of the catheter between the balloon and the distal tip is selectively occluded while the balance of the lumen is vented.

2. Description of the Related Art

Catheters have long been used in a wide variety of medical procedures in which the catheter is received in a bodily orifice to conduct fluid by way of the orifice. An example of one such procedure is known as retrograde cardioplegia solution perfusion. The catheter employed is provided with a selectively inflatable cuff or balloon adjacent to its distal tip, which is formed with one or more fluid outlets. When the distal tip and the balloon are inserted in the coronary sinus and are properly situated there, the balloon is inflated to occlude the sinus and to retain the catheter in it. Typically, the catheter and balloon are introduced in the coronary sinus as blood is naturally flowing through it in the opposite direction. Once the balloon has been inflated to occlude the sinus, cardioplegia solution is forced through the catheter to exit from the outlet at the distal tip and perfuse the heart by way of the cardiac veins.

Many different balloon catheter assemblies have been developed for this procedure, but they can be divided between those having manually inflated balloons and those provided with "self-inflating" or "auto-inflating" balloons. Manual inflation is accommodated by manufacturing the catheter assembly with a secondary lumen in communication with the interior of the balloon. Auto-inflating balloons are automatically inflated by means of a fluid interconnection between the catheter lumen and the interior of the balloon. The balloon may be preformed so that the body portion of the balloon extends radially outwardly from the catheter body even in the relaxed condition. Alternatively, the balloon may be formed of an elastomeric material such as silicone so that substantially the entire balloon is tightly received around the body of the catheter in the relaxed position and must be expanded as it is inflated in order to occlude the coronary sinus.

Examples of such catheters are disclosed in U.S. Pat. No. 5,385,548, issued Jan. 31, 1995 to C. R. Williams et al.; U.S. Pat. No. 5,197,952, issued Mar. 30, 1993 to S. J. Marcadis et al.; and U.S. Pat. No. 4,917,667, issued Apr. 17, 1990 to J. Jackson.

Prior catheter assemblies lack means for occluding the outlet at the distal tip of the catheter during insertion in the coronary sinus to prevent or restrict the flow of blood into the catheter lumen while simultaneously venting the balloon. Occlusion of the outlet serves the dual purpose of minimizing both fluid loss by the patient and the medical staff's contact with the patient's blood. Venting the balloon is advantageous in reducing the relatively high insertion force required to properly mount a preformed balloon-type catheter in the coronary sinus as the blood is naturally flowing therethrough. By lessening the insertion force, it is possible to reduce the degree of trauma suffered by the tissue of the coronary sinus during perfusion.

SUMMARY OF THE INVENTION

The catheter assembly according to the invention overcomes the problems of the prior art by selectively occluding a portion of the lumen of the catheter, thereby preventing the inadvertent flow of blood therethrough while simultaneously venting another portion of the catheter assembly so that the autoinflate balloon may be easily deflated upon insertion, thereby reducing the insertion force of the assembly.

The catheter assembly according to the invention comprises a catheter formed with a fluid-delivery lumen open at the proximal end of the catheter and extending through at least a portion of the length of the catheter thereof. The catheter has a distal end portion which is adapted to be received in a bodily orifice. An inflatable member is provided on an exterior surface of the catheter adjacent the distal end portion. At least one inflation aperture fluidly interconnects the fluid-delivery lumen and the interior of the inflatable member. At least one discharge aperture fluidly interconnects the fluid delivery lumen and the exterior of the catheter. In order to create a back pressure in the lumen and balloon, the effective area of the at least one discharge aperture is smaller than the effective area of the at least one inflation aperture. An introducer is selectively received in the fluid-delivery lumen by way of the proximal end thereof. Preferably, the introducer is slideably received in the lumen. An obturator is disposed within the fluid-delivery lumen on either the catheter or introducer. The obturator is provided intermediate the discharge aperture and the inflation aperture so that fluid cannot flow between these two apertures when the obturator is in place. The obturator is movable between an occluded condition inhibiting the flow of fluid in the fluid-delivery lumen between the two apertures during insertion of the catheter into the orifice and an unoccluded condition permitting the flow of fluid between the apertures. A vent is provided proximally of the obturator on either the catheter or introducer. The vent fluidly interconnects the interior of the inflatable member and the atmosphere to permit air entrapped within the inflatable member to be exhausted to the atmosphere during insertion of the distal end portion in a bodily orifice. The catheter assembly according to the invention provides for occlusion of a portion of the lumen thereby preventing blood from flowing into the balloon interior or through the lumen into contact with the medical personnel while also venting the balloon so that the balloon can be easily inserted into the coronary sinus with a minimum amount of insertion force. This structure provides two advantages, first, the trauma to the coronary sinus tissue is dramatically reduced due to a reduction in the required insertion force and second, the loss of blood and contact with the medical personnel is minimized.

While the preferred embodiment of the invention is ideally suited for use in a retrograde cardioplegia perfusion process, the invention is suitable for use in a wide variety of different applications in which a catheter is received in an orifice for the purpose of conducting fluid through the orifice.

A variety of structures for the vent are within the scope of the invention. For example, the vent can comprise a fluid conduit traversing at least a portion of the introducer wherein one end of the fluid conduit is in fluid communication with the lumen proximally of the obturator, and the other end of the fluid conduit is in fluid communication with the atmosphere. The fluid conduit can comprise a groove formed in the exterior surface of the collar or may comprise a channel extending through the body or interior of the collar. Alternatively, the vent can be formed from the space between a stiffening member and the introducer wire which is telescopically received therein, wherein this space is fluidly connected to the atmosphere. In another embodiment, the vent can comprise a secondary lumen having one end open to the fluid-delivery lumen and the other end open to atmosphere. In still another embodiment, the vent can be formed from a vent lumen wherein one end is open to the interior of the inflatable member and the other end is open to the atmosphere.

Several different embodiments of the obturator are within the scope of the invention. In one embodiment, the obturator comprises a plug member carried on the introducer wherein the plug is substantially complementary to the interior surface of the lumen. In another embodiment, the obturator comprises a one-way valve, such as a duckbill valve disposed in the fluid delivery system.

In view of the several different embodiments of the vent and obturator, the catheter assembly can have a variety of different structures. Virtually any of the obturator embodiments can be combined with virtually any of the vent embodiments for creating a catheter assembly within the scope of the invention.

These and other objects, features, and advantages of the invention will be apparent from the ensuing description in conjunction with the accompanying drawings.

DETAILED DESCRIPTION OF THE PREFERRED EMBODIMENTS

Figures 1, 2:
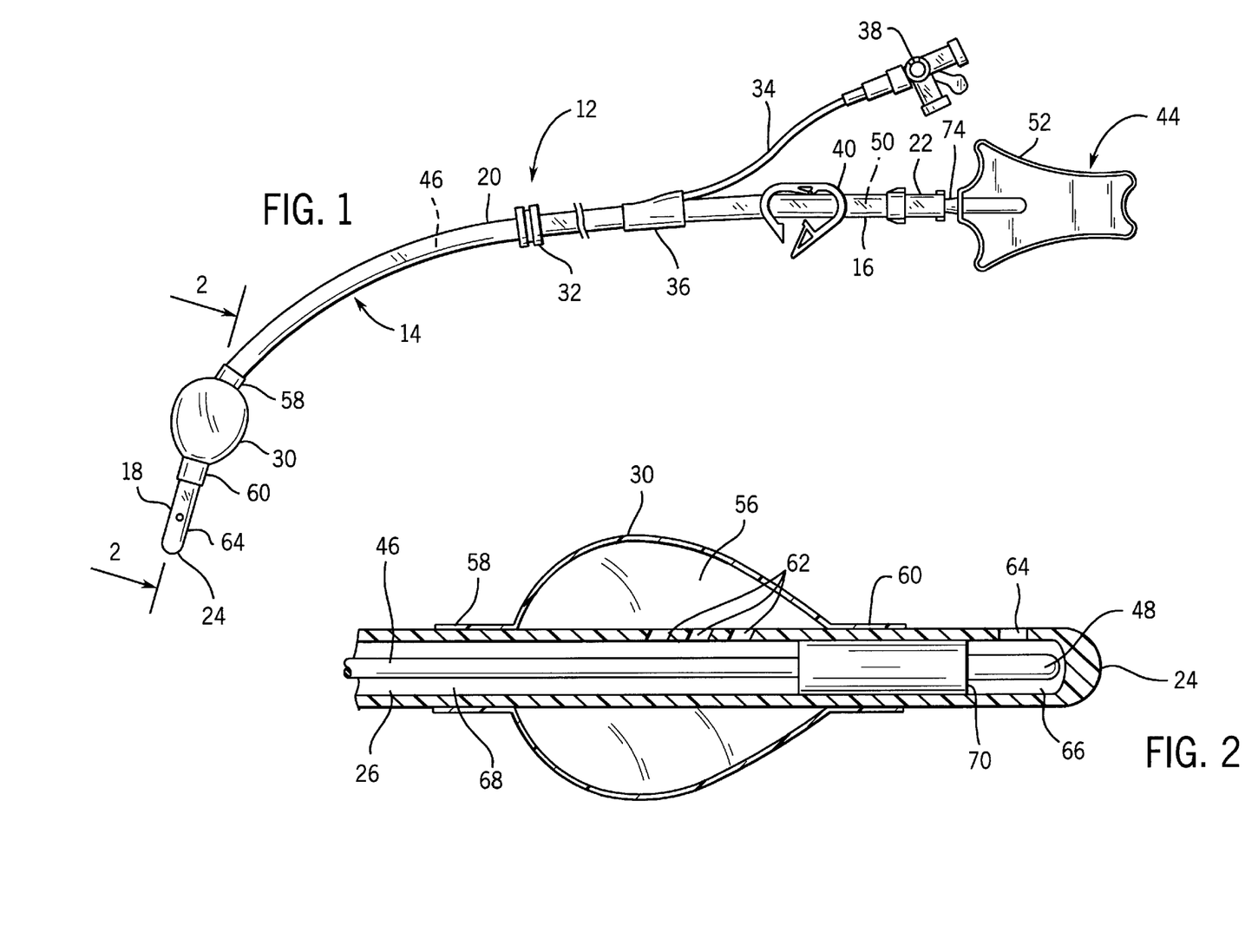
FIG. 1 is a perspective view of a catheter assembly according to the invention.
FIG. 2 is an enlarged, longitudinal, sectional view of the distal end portion of the catheter assembly, taken along line 2—2 of FIG. 1, showing one embodiment of the obturator means according to the invention with the distal end portion in an occluded condition.

Referring now to the drawings and to FIG. 1 in particular, a catheter assembly 12 according to the invention is shown. In this embodiment, the catheter assembly 12 comprises a catheter 14 having a proximal end 16, a distal end 18, and a body 20 intermediate the proximal and distal ends. A luer connector 22 is provided on the proximal end 16, and the distal end 18 is closed by a rounded tip 24. A primary lumen 26 extends from the rounded tip 24 to the luer connector 22, and an expandable member such as a balloon 30 is provided on the catheter 14 adjacent to the distal end 18. A conventional suture collar 32 is provided on the catheter body 20 and a conventional secondary lumen 34 is provided for measuring the fluid pressure at the distal end of the catheter 14. The secondary lumen 34 is in-molded into the side wall of the catheter body and surrounded, in part, by a sleeve 36. A conventional stopcock valve 38 is provided on the terminal end of the lumen 34. A conventional clamp 40 is provided on the catheter 14 intermediate the sleeve 36 and the luer connector 22 for clamping closed the primary lumen 26.

A stylet or introducer 44 is selectively, telescopically received in the catheter primary lumen 26 to provide strength and rigidity to the catheter during insertion of the catheter assembly 12 into the coronary sinus. The introducer comprises a substantially rigid body 46 having a distal end 48, a proximal end 50, and a handle 52 secured to the proximal end 50. A frusto-conically-shaped collar 74 extends distally from the handle 52 at the junction between the handle 52 and the proximal end 50 of the introducer 44. The collar 74 is dimensioned so that at least a portion of the collar 74 is tightly received inside the open end of the luer connector 22 of the catheter 14. Once the distal end 18 of the catheter and the balloon 30 are properly positioned in the coronary sinus, the introducer 44 is slideably removed from the catheter 14. Finally, the catheter 14 is connected to conventional cardioplegia perfusion equipment for performing the perfusion process. As perfusion fluid flows distally through the catheter, the balloon is automatically inflated to occlude the coronary sinus and retain the catheter therein.

As noted above, the catheter assembly 12 is typically inserted into the coronary sinus as the heart beats regularly and the blood flows therethrough. This dynamic state for the heart presents several problems in securing the catheter assembly therein, and these problems become more pronounced when using an automatically inflated balloon as depicted in FIGS. 1 and 2. In this embodiment, the balloon 30 comprises a hollow body portion 56 and proximal and distal retention collars 58, 60 which are securely adhered to the outside surface of the catheter 14. The hollow interior of the body of the balloon 56 is fluidly interconnected with the catheter primary lumen 26 by at least one balloon aperture 62 formed in the catheter 14. At least one catheter discharge aperture 64 is formed in the catheter 14 further down the fluid flow path of the primary lumen 26. Preferably, the cross-sectional area of the catheter discharge apertures 64 is less than the cross-sectional area of the balloon apertures 62 so that back pressure is created in the primary lumen 26 and hollow balloon body 56 sufficient to inflate the balloon 30 without rupturing. Other examples of auto-inflating balloon catheters are disclosed in the aforementioned U.S. Pat. No. 5,385,548 to Williams et al. which is expressly incorporated herein by reference.

Use of a preformed, auto-inflating balloon on a retrograde cardioplegia solution perfusion catheter presents significant challenges as noted above. The first problem to be solved is to successfully occlude the flow of fluid through the catheter primary lumen 26 between the balloon apertures 62 and catheter discharge apertures during the step of inserting the catheter assembly 12 into the coronary sinus. As the distal end of the catheter assembly is inserted into the coronary sinus and encounters the pressurized blood flow therein, this pressurized fluid must be prevented from entering the balloon. The catheter assembly 12, according to the invention, includes obturator means to prevent fluid such as blood from prematurely entering the primary lumen 26 and balloon body 56.

The first embodiment of the obturator means is seen in FIG. 2 in which the obturator means comprises a solid member or plug 70 provided on the introducer 44 adjacent to the distal end 48 of the introducer body. The plug 70 is substantially complementary to the hollow interior of the catheter 14 and positioned on the introducer 44 so that the plug 70 is positioned between the catheter discharge apertures 64 and the balloon apertures 62 when the introducer 44 is fully and properly received inside the catheter 14. Preferably, the outside diameter of the plug 70 closely approximates the inside diameter of the catheter 14 so that fluid flow through the primary lumen 26 is effectively prevented thereby creating a distal lumen chamber 66 and a proximal lumen chamber 68. With the plug 70 properly positioned in the primary lumen 26, any pressurized fluid entering the distal lumen chamber 68 through the catheter discharge apertures 64 is stopped from prematurely inflating the balloon 56.

Figure 3:
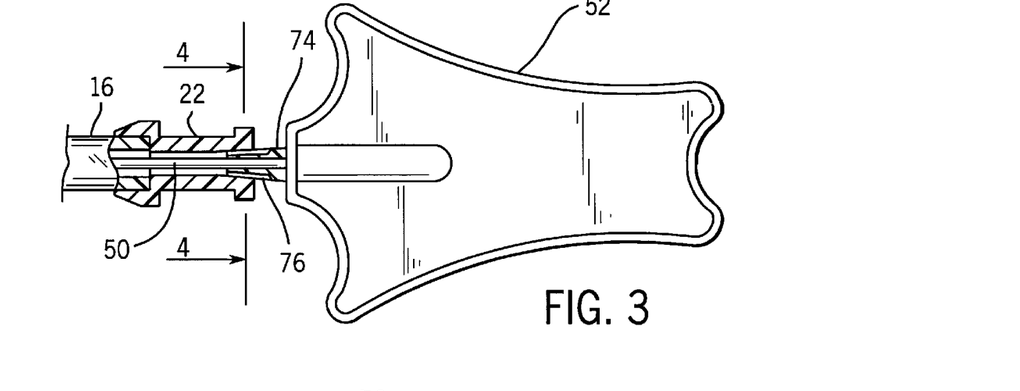
FIG. 3 is an enlarged, longitudinal, sectional view of the proximal end portion of the catheter assembly of FIG. 1, showing one embodiment of means for venting the catheter assembly according to the invention.
Figure 4:
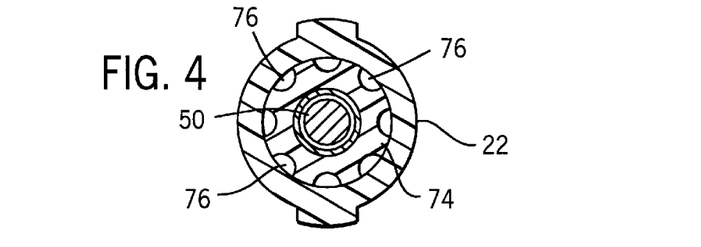
FIG. 4 is a cross-sectional view of the catheter assembly of FIG. 3, taken along line 4—4 thereof.

As noted above, preformed balloons typically assume an expanded position in the relaxed state similar to that seen in FIG. 2. This expanded position is often larger than the diameter of the coronary sinus. In order to minimize the trauma suffered by the tissue of the coronary sinus during insertion of the catheter assembly, means must be provided to vent the balloon so that the balloon may collapse without resistance during insertion. The catheter assembly 12, according to the invention, includes several different embodiments for venting the air entrapped in the balloon. The first embodiment of the vent means is seen in FIGS. 3 and 4 in which the introducer handle 52 includes the integrally formed frusto-conical collar 74 which is tightly received inside the luer connector 22 of the catheter 14. The collar 74 has at least one groove or channel 76 formed thereon to establish fluid communication between the proximal lumen chamber 68 of the catheter 14 and the atmosphere. Preferably, multiple grooves 76 are formed on the outside surface of the collar 74 and extend a sufficient distance along the length of the collar 74 to ensure fluid communication between the proximal lumen chamber 68 and the atmosphere.

With the combination of the obturator means or plug 70 as seen in FIG. 2 and the vent means or grooves 76 as seen in FIGS. 3 and 4, the catheter assembly may be quickly and easily inserted into the coronary sinus with a minimum of effort and trauma to the tissue of the coronary sinus while simultaneously minimizing the patient's blood loss and contact between the health care workers and the blood. Testing has shown that the force required to insert the catheter assembly according to the invention into the coronary sinus is reduced over 70% as compared to the force required to insert a conventional retrograde cardioplegia solution perfusion catheter with a preformed, auto-inflating balloon which does not include the obturator and vent means. This dramatic reduction in the insertion force will minimize trauma to the tissue of the coronary sinus while simultaneously minimizing blood loss and contact with the medical staff.

Figure 5:
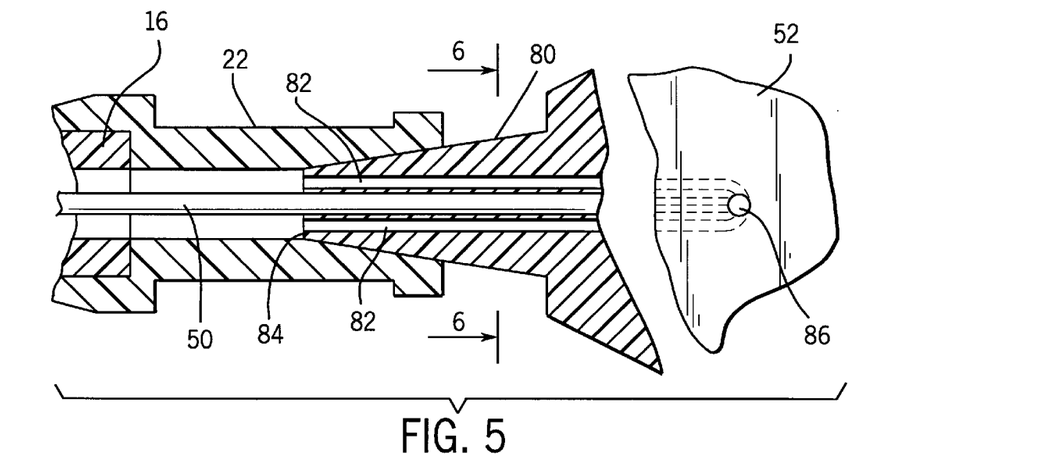
FIG. 5 is a greatly enlarged, partial, longitudinal, sectional view of the proximal end portion of a catheter assembly similar to the catheter assembly of FIG. 1 showing a second embodiment of the venting means according to the invention.
Figure 6:
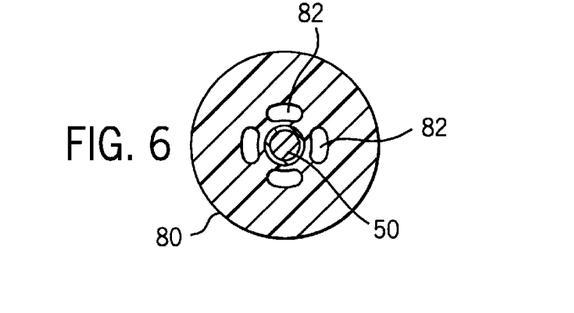
FIG. 6 is a cross-sectional view of the catheter assembly of FIG. 5, taken along line 6—6 thereof.

A second embodiment of the vent means is shown in FIGS. 5 and 6. In this embodiment, the introducer handle 52 comprises a conically-shaped collar 80 integrally formed therewith and extending distally therefrom which is telescopically received in the luer connector 22 and creates an airtight seal therewith. At least one internal channel 82 is integrally formed in the collar so that one end of the channel 82 passes through an end wall 84 of the collar 80 thereby establishing fluid communication between the proximal lumen chamber 68 and the internal channel 82. The other end of the channel 82 terminates at an aperture 86 formed in the side wall of the handle 52, establishing fluid communication between the internal channel 82 and the atmosphere. In this embodiment, air forced from the balloon 30 passes through the primary lumen 26 into the internal channels 82 and is exhausted to the atmosphere through the aperture 86 provided in the introducer handle 52 so that the catheter assembly 12 may be easily inserted into the coronary sinus.

Figure 7:
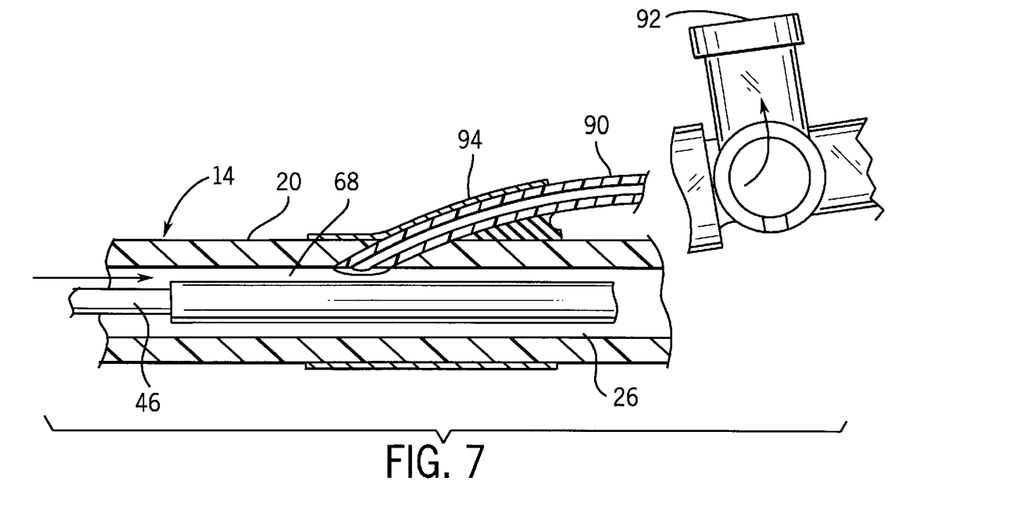
FIG. 7 is a greatly enlarged, longitudinal, sectional view of an intermediate portion of a catheter assembly similar to the catheter assembly of FIG. 1 showing a third embodiment of the venting means according to the invention.

A third embodiment of the vent means is seen in FIG. 7. In this embodiment, a secondary lumen 90 is tapped into the body 20 of the catheter and specifically, the proximal lumen chamber 68 when the introducer 44 and obturator means are received therein. A conventional valve such as a stopcock valve 92 is provided on the terminal end of the secondary lumen 90 for selectively opening and closing the secondary lumen 90. A protective sleeve 94 preferably surrounds the secondary lumen 90 at the mounting of the secondary lumen 90 and catheter body 20. In this embodiment, as entrapped air is forced from the balloon 30 into the catheter primary lumen 26, the air is vented to the atmosphere from the proximal lumen chamber 68 of the primary lumen 26 through the secondary lumen 90 and the open stopcock valve 92. Although not shown in FIG. 7, it would be anticipated that the conical collar of the introducer handle 52 would effectively seal the luer connector 22 of the catheter 14, preventing air from escaping the primary lumen 26, the only air outlet would be through the secondary lumen 90.

Figure 8:
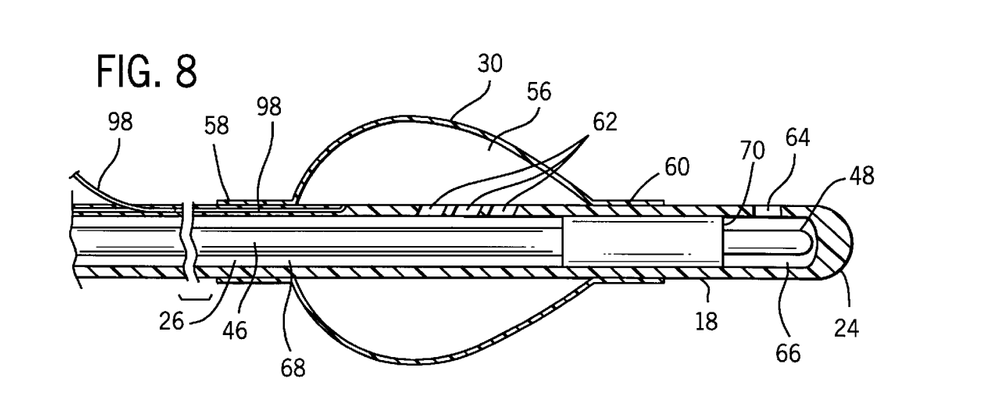
FIG. 8 is a view similar to FIG. 2 but showing a fourth embodiment of the venting means according to the invention.

A fourth embodiment for the vent means is shown in FIG. 8. In this embodiment, a secondary lumen 98 is integrally formed into the body 20 of the catheter 12 in which one end of the lumen 98 is fluidly connected to the body of the hollow balloon body 56 and the other end of the lumen passes through the side wall of the catheter 14 in a conventional manner to a conventional stopcock valve (not shown) mounted at its terminal end. In this embodiment, it is again anticipated that the proximal end of the catheter primary lumen 26 would be effectively sealed as a result of the friction fit of the handle collar 74 and the luer connector 22. Therefore, the only outlet for the air from the balloon body 56 would be through the secondary lumen 98 and stopcock valve. Once the balloon 30 is properly inserted in the coronary sinus and ready for inflation, the stopcock valve would be closed and the autoinflating balloon 30 would inflate as a result of the flow of pressurized fluid through the primary lumen 26 and the apertures of the balloon and catheter 62, 64, respectively.

Figure 9:
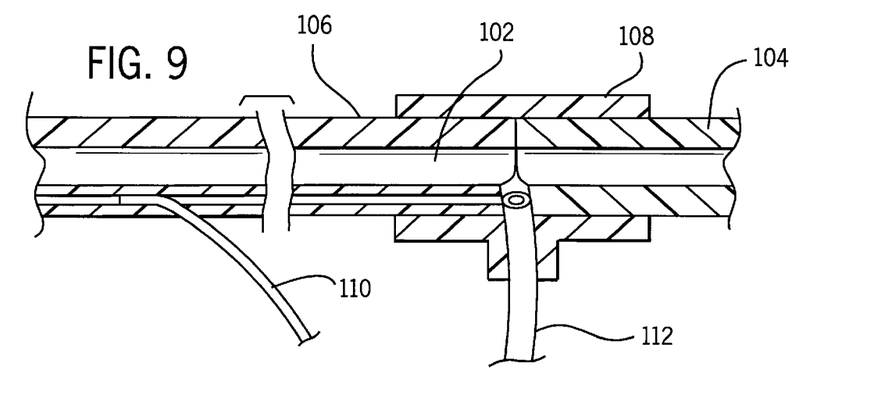
FIG. 9 is an enlarged, longitudinal, sectional view of an intermediate portion of a catheter assembly similar to the catheter assembly of FIG. 1 showing a fifth embodiment of the venting means according to the invention.

Yet another embodiment of the vent means is shown in FIG. 9. In this fifth embodiment, the catheter comprises a composite of a single lumen catheter portion 104 and a multi-lumen catheter portion 106. The ends of the two catheter portions 104, 106 are joined to one another by a conventional connector 108 and the primary lumen 102 of the catheter is defined by the lumen of the single lumen catheter 104 and multi-lumen catheter 106. Such hybrid catheters are often used so that effective clamping of the catheter lumen 102 may be achieved. In some instances, the multi-lumen catheters are difficult to create an effective, fluid-tight seal with conventional clamps.

In the fifth embodiment, a conventional secondary pressure sensing lumen 110 extends outwardly from the multi-lumen catheter portion 106. In addition, a vent lumen 112 extends radially outwardly from the primary catheter lumen 102, one end of the vent lumen 112 being fluidly connected to the primary catheter lumen 102 and the other end of the vent lumen 112 being connected to conventional valve means such as a stopcock valve which may be selectively opened and closed (not shown).

In this embodiment, air is exhausted from the balloon by first opening the stopcock valve on the vent lumen 112. Entrapped air is forced from the balloon 30 into the primary lumen 102 which in turn is vented to the atmosphere through the vent lumen 112 and stopcock valve (not shown). Once again, it is anticipated in this embodiment that the only air outlet from the primary lumen when the introducer is received therein would be through the vent lumen 112.

Figure 10:
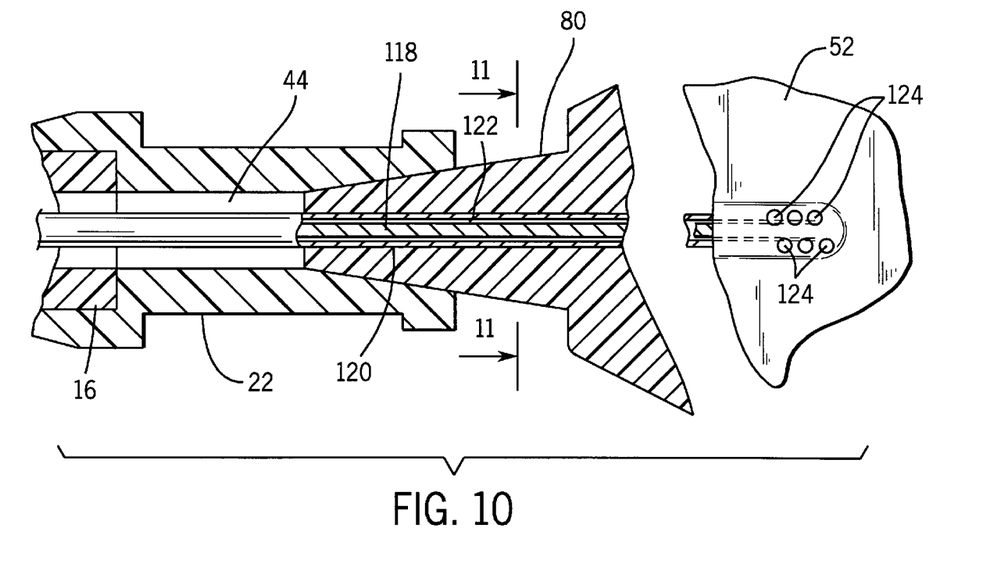
FIG. 10 is a view similar to FIG. 5 but showing a sixth embodiment of the venting means according to the invention.
Figure 11:
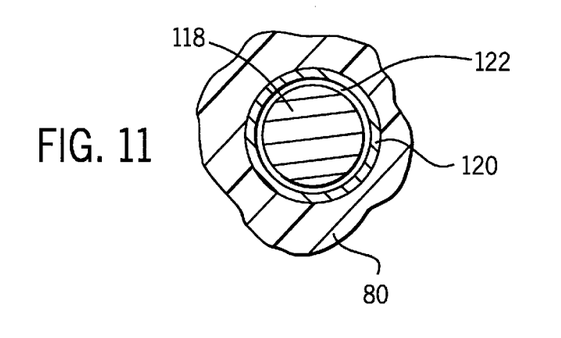
FIG. 11 is a cross-sectional view of the catheter assembly of FIG. 10 taken along line 11—11 of FIG. 10.

A sixth embodiment of the vent means is shown in FIGS. 10 and 11. In this embodiment, the introducer 44 comprises a central wire 118 and a stiffener element 120 telescopically surrounding the wire 118. The outside diameter of the central wire 118 is less than the inside diameter of the stiffener sleeve 120 so that an air space 122 is defined between the wire and sleeve. The length of the stiffener element 120 is less than that of the wire 118 and the distal end of the stiffener sleeve 120 is open so that the wire 118 extends therethrough. With this structure, air may freely pass from the primary lumen 26 into the air space 122 between the wire 118 and sleeve 120. The introducer handle 52 which mounts both the wire 118 and sleeve 120 has a plurality of apertures 124 formed therein which extend from the exterior surface of the handle 52 through the stiffener sleeve 120 to the air space 122 between the wire 118 and sleeve 120. Therefore, as air is forced from the balloon 30 during insertion of the catheter assembly 12 into the coronary sinus, the air passes from the hollow balloon body 56, through the balloon apertures 62, and into the primary lumen 26. Next, the pressurized air flows into the air space 122 between the stiffener sleeve 120 and wire 118 and is exhausted to the atmosphere through the apertures 124 provided in the introducer handle 52.

Figure 12:
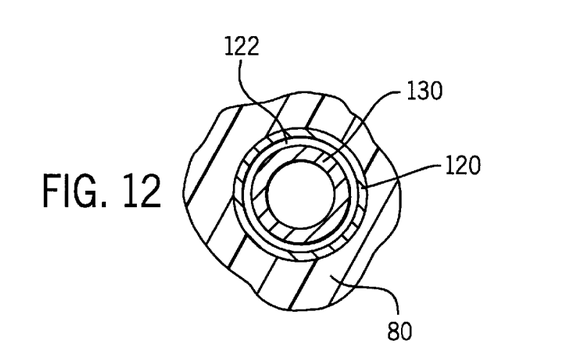
FIG. 12 is a view similar to FIG. 11 but showing a seventh embodiment of the venting means according to the invention.

FIG. 12 shows a seventh embodiment of the vent means which is merely an adaptation of the sixth embodiment seen in FIGS. 10 and 11. In this embodiment, the central wire 130 is hollow and at least one aperture is formed in the wire 130 interconnecting the hollow interior and proximal lumen chamber 68. Therefore, as air is forced from the hollow balloon body 56 into the primary lumen 26 and proximal lumen chamber, the air passes into both the hollow central wire 130 and the air space of the hollow stiffener sleeve 120 and is vented to the atmosphere through apertures 124 in the introducer handle. In this embodiment, the apertures 124 extend though the proximal ends of both the stiffener sleeve 120 and hollow central wire 130. An alternative to forming apertures in the sleeve 120 and wire 130 would be to create a manifold in the body of the handle 52 in which the proximal ends of the hollow central wire 130 and hollow stiffener sleeve 120 would fluidly connect with the manifold and the apertures 124 would extend through the introducer handle 52 into the hollow manifold of the handle 52.

Figure 13:
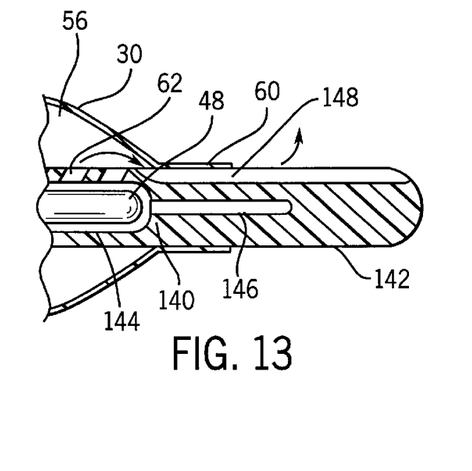
FIG. 13 is an enlarged, partial, longitudinal, sectional view of the distal end portion of a catheter assembly similar to the catheter assembly of FIG. 1 showing a second embodiment of obturator means according to the invention with the distal end portion in an unoccluded condition.
Figure 14:
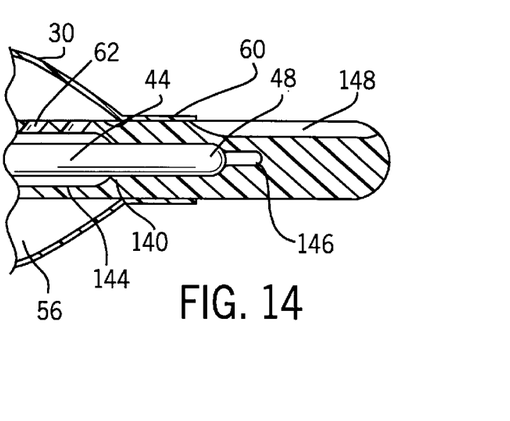
FIG. 14 is a view similar to FIG. 13 but showing the distal end portion of the catheter assembly of FIG. 13 in an occluded condition.

FIGS. 1 and 2 show the first embodiment of the obturator means for the catheter assembly according to the invention. A second embodiment of the obturator means is seen in FIGS. 13 and 14. In this embodiment, the distal end 142 of the catheter comprises a lumen of varying diameter. A first portion 144 of the lumen has a diameter which exceeds the diameter of the body of the introducer 46 and a second portion 146 of the lumen has a diameter less than that of the body of the introducer 46. However, the diameter of the second portion 146 is not so small so that the distal end 48 of the introducer body 46 cannot be forcefully received therein. The catheter is preferably formed from a pliable, elastomeric material sufficient to permit deformation of the catheter.

In this embodiment of the obturator means, the fluid flow path for the pressurized cardioplegia solution from the lumen is modified over earlier embodiments. The fluid flows from the first portion 144 of the lumen into the hollow body 56 of the balloon 30 through the balloon apertures 62. At least one discharge channel 148 is formed in the side wall of the catheter 140 adjacent to the second portion 146 of the lumen. One end of the discharge channel 148 is in fluid communication with the hollow interior of the balloon 30 and the other end of the channel is open to the atmosphere on the distal end 142 of the catheter.

Prior to insertion into the coronary sinus, the introducer 44 is inserted into the lumen of the catheter 140 a sufficient distance so that the distal end 48 of the introducer 44 is forcibly received in the pliable, distal end 142 of the catheter 140. As the introducer 44 is forced into the second portion 146 of the lumen, the body of the catheter 140 is displaced outwardly a sufficient distance to seal or pinch closed the discharge channel 148 against the balloon 30. Once the discharge channel 148 has been pinched closed, then the distal end 142 of the catheter 140 may be inserted into the coronary sinus and blood will be prevented from entering the balloon 30 as a result of the expansion of the distal end 142 of the catheter 140 thereby closing the discharge channel 148. Once the catheter 140 and balloon 30 are properly positioned, the introducer 46 is withdrawn from the first and second portions of the lumen 144, 146, respectively, and the retrograde cardioplegia perfusion fluid may freely flow through the first portion of the lumen 144 through the balloon apertures 62 into the balloon 30 and exit the catheter assembly through the discharge channel 148.

The second obturator means seen in FIGS. 13 and 14 may be modified by replacing the discharge channel 148 with one or more apertures extending through the catheter to fluidly interconnect the second portion 146 of the lumen with the atmosphere. Insertion of the distal end 48 of the introducer body 46 into the second portion 146 of the lumen would effectively seal the first portion of the lumen 144 from the second portion of the lumen 146 thereby preventing premature inflation of the balloon or entry of fluid into the primary lumen.

Figure 15:
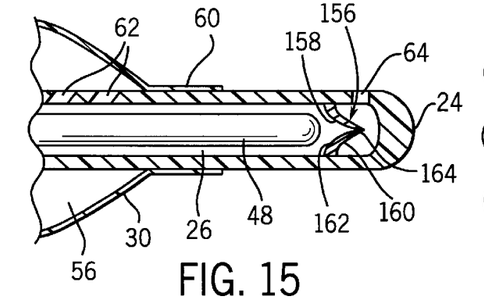
FIG. 15 is a view similar to FIG. 14 but showing a third embodiment of obturator means according to the invention with the distal end portion of the catheter assembly in an occluded condition.
Figure 16:
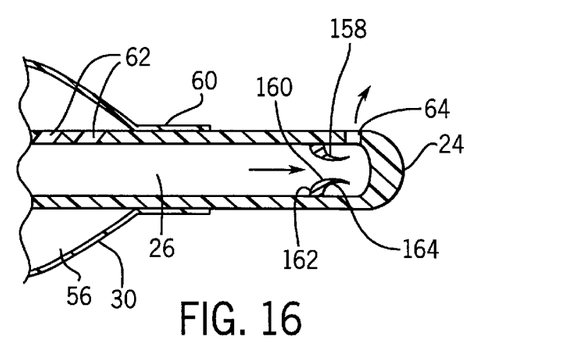
FIG. 16 is a view similar to FIG. 15 but showing the distal end portion of the catheter assembly of FIG. 15 in an unoccluded condition.

A third embodiment of the obturator means is seen in FIGS. 15 and 16. In this embodiment, a duckbill valve 156 is provided inside the hollow interior of the primary lumen 26 between the balloon apertures 62 and catheter discharge apertures 64. The duckbill valve 156 is formed from first and second valve members 158, 160. Each valve member comprises a broad base 162 and a distally extending, tapered tip 164. The broad base 162 is secured to the inside surface of the lumen by conventional means and the tips 164 extend distally and inwardly to abut one another in the relaxed position. In the event that pressurized fluid enters the primary lumen 26 through the catheter discharge apertures 64, the tapered, pinched structure of the duckbill valve 156 will prevent the flow of fluid upstream, through the primary lumen 26. As pressurized fluid is forced distally through the primary lumen 26 during the retrograde perfusion process, the pressurized fluid will inflate the balloon through the balloon aperture 62 and deform the first and second valve members 158, 160 to the open position, as seen in FIG. 16. Once the valve 156 is open, pressurized fluid will exit the catheter through the catheter discharge aperture 64.

Figure 17:
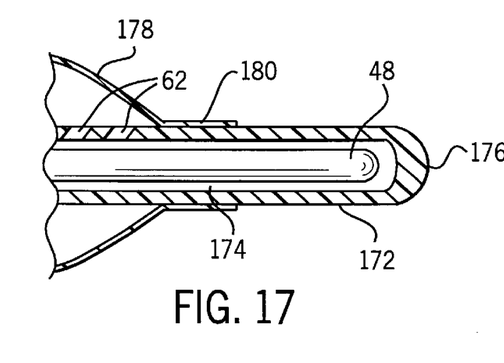
FIG. 17 is a view similar to FIG. 14 or FIG. 15 but showing a fourth embodiment of obturator means according to the invention with the distal end portion of the catheter assembly in an occluded condition.
Figure 18:
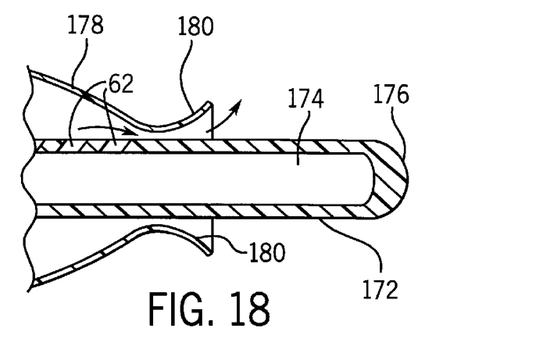
FIG. 18 is a view similar to FIG. 17 but showing the distal end portion of the catheter assembly of FIG. 17 in an unoccluded condition.

A fourth embodiment of the obturator means is seen in FIGS. 17 and 18. In this embodiment, the catheter 172 does not include a discharge aperture formed in the body of the catheter as seen in the earlier embodiments. In this embodiment, the proximal end of the balloon 178 is securely adhered to the outside surface of the catheter body 172 as previously discussed with respect to the proximal retention collar 58. However, at least a portion of the distal end 180 of the balloon 178 is not secured to the outside surface of the catheter 172. Therefore, as the fluid flows through the catheter lumen 174 to the distal tip 176 of the catheter 172, the fluid enters the hollow interior of the balloon 178. When sufficient pressure is established inside the balloon, the portion of the balloon distal end 180 which is not securely adhered to the outside surface of the catheter 172 will deflect radially outwardly permitting the flow of fluid from the balloon 178 to the atmosphere. In this embodiment, the balloon material 178 must be selected so that the deformation of the distal end of the balloon is achieved only when the proper fluid pressure is established inside the hollow interior of the balloon 178.

Blood is prevented from flowing backwardly into the balloon 178 as the catheter assembly is inserted into the coronary sinus as a function of the structure of the balloon 178 and the elasticity of the balloon material. Blood will enter the balloon 178 only if the blood flow may forcibly deform the distal end 180 of the balloon 178 with respect to the catheter 172. In view of the fluid pressure encountered in the coronary sinus, such deformation of the balloon 178 is improbable.

Figure 19:
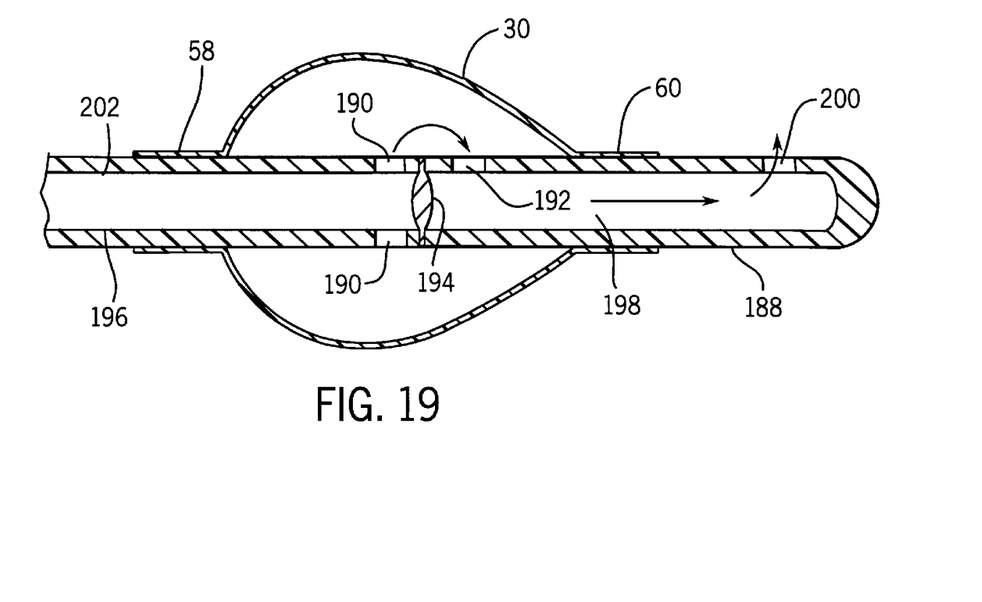
FIG. 19 is a view similar to FIG. 2, but showing a fifth embodiment of obturator means according to the invention with the distal end portion of the catheter assembly in an unoccluded condition.
Figure 20:
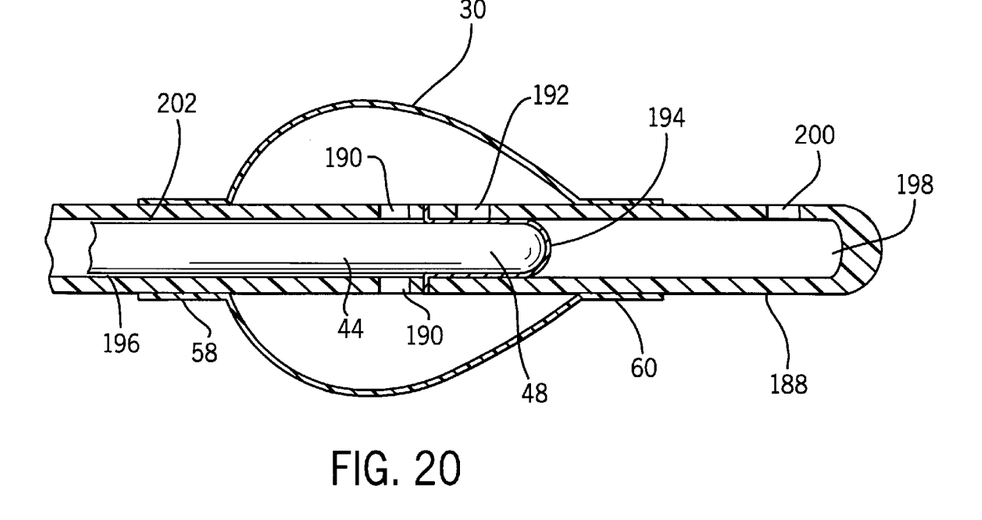
FIG. 20 is a view similar to FIG. 19, but showing the distal end portion of the catheter assembly of FIG. 19 in an occluded condition.

FIGS. 19 and 20 depict a fifth embodiment of the obturator means. In this embodiment, the balloon 30 surrounds balloon supply apertures 190 and balloon discharge apertures 192. The cross-sectional area of the balloon supply apertures 190 is greater than the discharge apertures 192 so that a back pressure is created inside the balloon 30 as fluid flows distally. A pliable, preferably elastomeric valve member 194 is mounted inside the lumen 196 of the catheter 188 intermediate the balloon supply apertures 190 and discharge aperture 192. The valve member 194 effectively blocks the flow of fluid through the lumen 196 and forces the fluid to pass through the balloon 30 via the apertures 190, 192 before discharge from the outlet aperture 200. The valve member 194 divides the lumen 196 into a distal lumen chamber 198 and a proximal lumen chamber 202.

In use, the introducer 44 is received inside the lumen 196 until the distal end 48 of the introducer body 46 contacts the valve member 194. The introducer 44 is inserted further into the catheter a sufficient distance until the distal end 48 of the introducer 44 and the valve member 194 extend distally of the balloon discharge aperture 192. Preferably, the introducer is dimensioned so that the diameter of the introducer body 46, in addition to the thickness of the valve member 194 will effectively seal the interior of the catheter lumen, thereby preventing the back flow of blood from the distal lumen chamber 198 through the discharge aperture 192 to the hollow interior of the balloon 30 during insertion of the catheter assembly into the coronary sinus. When the catheter and balloon are properly positioned in the coronary sinus, the introducer 44 is withdrawn and the valve member 194 returns to its relaxed position. Pressurized perfusion fluid flows through the primary lumen 196 and bypasses the valve member 194 by flowing through the balloon 30, into the distal lumen chamber 198 and ultimately out of the catheter 188 through the outlet aperture 200. The spacing of the balloon supply 190 and discharge apertures 192 and the materials selected for the valve member 194 must be coordinated so that the pressure of the perfusion fluid flowing through the lumen 196 would not be sufficient to deform the valve member 194 to a point that the valve member 194 would occlude the balloon discharge aperture 192 during the perfusion process.

As is evident from the description above, the invention comprises several different embodiments of the obturator means and vent means. It is anticipated that a wide variety of differing catheter assembly structures could be created by the several possible combinations of the various vent and obturator means. In other words, any of the vent means may be incorporated into a catheter assembly with any of the obturator means.

The preferred use of the variable catheter structures described above is for a retrograde cardioplegia perfusion process. However, the invention is not limited to such applications. The catheter assembly according to the invention is suitable for any application in which a catheter is received in an orifice and both occlusion of the distal end and venting of the expandable member are desirable.

While the invention has been particularly described in connection with certain specific embodiments thereof, it is to be understood that this is by way of illustration and not of limitation, and the scope of the appended claims should be construed as broadly as the prior art will permit.

What is claimed is:

1. A catheter assembly comprising:
   a catheter formed with a fluid-delivery lumen open at the proximal end of the catheter and extending through at least a portion of the length thereof, the catheter having a distal end portion adapted to be received in a bodily orifice, an inflatable member on an exterior surface of the catheter at the distal end portion, at least one inflation aperture fluidly interconnecting the fluid-delivery lumen and the interior of the inflatable member, and at least one discharge aperture fluidly interconnecting the fluid-delivery lumen and the exterior of the catheter, the effective area of the at least one discharge aperture being smaller than the effective area of the at least one inflation aperture;

an introducer received in the fluid-delivery lumen by way of the proximal end thereof and slidably removable therefrom;

an obturator disposed within the fluid-delivery lumen intermediate the at least one discharge aperture and the at least one inflation aperture, the obturator being movable between an occluded condition inhibiting flow of fluid in the fluid-delivery lumen between the at least one discharge aperture and the at least one inflation aperture during insertion of the distal end portion in the orifice and an unoccluded condition permitting flow of fluid therebetween upon removal of the obturator from the fluid-delivery lumen; and a vent provided in one of the catheter and introducer, proximally of the obturator, and fluidly interconnecting the interior of the inflatable member and the atmosphere to permit air entrapped within the inflatable member to be exhausted to the atmosphere during insertion of the distal end portion in a bodily orifice.

2. A catheter assembly according to claim 1, wherein the vent comprises a fluid conduit traversing at least a portion of the introducer, one end of the fluid conduit being in fluid communication with the fluid-delivery lumen proximally of the obturator and the other end being in fluid communication with the atmosphere.

3. A catheter assembly according to claim 2, wherein the introducer includes a collar disposed in the proximal end of the fluid-delivery lumen when the introducer is fully seated therein, the fluid conduit being formed in the collar.

4. A catheter assembly according to claim 3, wherein the fluid conduit comprises a groove formed in an exterior surface of the collar.

5. A catheter assembly according to claim 3, wherein the fluid conduit extends through the interior of the collar.

6. A catheter assembly according to claim 5, wherein the introducer includes a handle at the proximal end thereof adjacent to the collar, the fluid conduit extending from the collar into the handle and terminating in a vent aperture open to the atmosphere formed in the handle at said other end of the fluid conduit.

7. A catheter assembly according to claim 2, wherein the introducer comprises a hollow first member having a predetermined internal diameter and a second member having a predetermined external diameter smaller than the internal diameter of the first member, at least a portion of the second member being telescopically received inside the hollow first member to establish between the first and second members a space comprising the fluid conduit, one end of the space being open to the fluid-delivery lumen when the introducer is fully seated in the catheter and the other end of the space being open to the atmosphere.

8. A catheter assembly according to claim 1, wherein the vent comprises a secondary lumen, at least a portion of the secondary lumen extending through the catheter, the secondary lumen having one end thereof open to the fluid-delivery lumen and a second end open to the atmosphere.

9. A catheter assembly according to claim 8, including a valve member associated with the secondary lumen, the valve member being selectively operable to close the secondary lumen to the flow of fluid between the catheter fluid-delivery lumen and the atmosphere.

10. A catheter assembly according to claim 1, wherein the vent comprises a vent lumen, at least a portion of the vent lumen being formed in the catheter and having one end thereof opening to the interior of the inflatable member and the other end opening to the atmosphere.

11. A catheter assembly according to claim 10, including a valve member associated with the vent lumen and spaced from the inflatable member for selectively closing the vent lumen to fluid flow.

12. A catheter assembly according to claim 1, wherein the catheter comprises a first member having a first lumen portion formed therein, a second member having a second lumen portion formed therein, and a connector joining the first and second members to each other longitudinally with the lumen portions fluidly connected to form the fluid-delivery lumen, the vent comprising a secondary lumen carried by the connector and having one end thereof in fluid communication with the fluid-delivery lumen and the other end thereof fluidly connected to the atmosphere.

13. A catheter assembly according to claim 12, including a valve member associated with the secondary lumen, the valve member being selectively operable to close the secondary lumen to the flow of fluid between the fluid-delivery lumen and the atmosphere.

14. A catheter assembly according to claim 1, wherein the obturator comprises a plug member carried on the introducer, the plug member being substantially complementary to the interior surface of the lumen.

15. A catheter assembly according to claim 1, wherein the obturator comprises a one-way valve disposed in the fluid-delivery lumen.

16. A catheter assembly according to claim 15, wherein the one-way valve comprises a duckbill valve.

17. A catheter assembly according to claim 1, wherein the at least one discharge aperture comprises at least a portion of the distal end of the inflatable member unattached to the exterior of the catheter.

18. A catheter assembly comprising:
a catheter formed with a fluid-delivery lumen open at the proximal end of the catheter and extending through at least a portion of the length thereof, the catheter having a distal end portion adapted to be received in a bodily orifice, an inflatable member on an exterior surface of the catheter at the distal end portion, at least one inflation aperture fluidly interconnecting the fluid-delivery lumen and the interior of the inflatable member, and at least one discharge aperture fluidly interconnecting the fluid-delivery lumen and the exterior of the catheter, the effective area of the at least one discharge aperture being smaller than the effective area of the at least one inflation aperture;

an obturator disposed within the fluid-delivery lumen intermediate the at least one discharge aperture and the at least one inflation aperture, the obturator being movable between an occluded condition inhibiting flow of fluid in the fluid-delivery lumen between the at least one discharge aperture and the at least one inflation aperture during insertion of the distal end portion in the orifice and an unoccluded condition permitting flow of fluid therebetween upon removal of the obturator from the fluid-delivery lumen;

a vent provided proximally of the obturator and fluidly interconnecting the interior of the inflatable member and the atmosphere to permit air entrapped within the inflatable member to be exhausted to the atmosphere during insertion of the distal end portion in a bodily orifice, the vent including a fluid conduit traversing at least a portion of the introducer, one end of the fluid conduit being in fluid communication with the fluid-delivery lumen proximally of the obturator and the other end being in fluid communication with the atmosphere; and an introducer received in the fluid-delivery lumen by way of the proximal end thereof and slidably removable therefrom, the introducer including a collar disposed in the proximal end of the fluid-delivery lumen when the introducer is fully seated therein, the fluid conduit being formed in the collar.

19. A catheter assembly according to claim 18, wherein the fluid conduit comprises a groove formed in an exterior surface of the collar.

20. A catheter assembly according to claim 18, wherein the fluid conduit extends through the interior of the collar.

21. A catheter assembly according to claim 20, wherein the introducer includes a handle at the proximal end thereof adjacent to the collar, the fluid conduit extending from the collar into the handle and terminating in a vent aperture open to the atmosphere formed in the handle at said other end of the fluid conduit.

22. A catheter assembly comprising:

a catheter formed with a fluid-delivery lumen open at the proximal end of the catheter and extending through at least a portion of the length thereof, the catheter having a distal end portion adapted to be received in a bodily orifice, an inflatable member on an exterior surface of the catheter at the distal end portion, at least one inflation aperture fluidly interconnecting the fluid-delivery lumen and the interior of the inflatable member, and at least one discharge aperture fluidly interconnecting the fluid-delivery lumen and the exterior of the catheter, the effective area of the at least one discharge aperture being smaller than the effective area of the at least one inflation aperture;

an introducer received in the fluid-delivery lumen by way of the proximal end thereof and slidably removable therefrom, the introducer including a hollow first member having a predetermined internal diameter and a second member having a predetermined external diameter smaller than the internal diameter of the first member;

an obturator disposed within the fluid-delivery lumen intermediate the at least one discharge aperture and the at least one inflation aperture, the obturator being movable between an occluded condition inhibiting flow of fluid in the fluid-delivery lumen between the at least one discharge aperture and the at least one inflation aperture during insertion of the distal end portion in the orifice and an unoccluded condition permitting flow of fluid therebetween upon removal of the obturator from the fluid-delivery lumen; and a vent provided proximally of the obturator and fluidly interconnecting the interior of the inflatable member and the atmosphere to permit air entrapped within the inflatable member to be exhausted to the atmosphere during insertion of the distal end portion in a bodily orifice, the vent including a fluid conduit traversing at least a portion of the introducer, wherein at least a portion of the second member of the introducer is telescopically received inside the hollow first member to establish between the first and second members a space comprising the fluid conduit, one end of the space being open to the fluid delivery lumen when the introducer is fully seated in the catheter and the other end of the space being open to the atmosphere.

23. A catheter assembly comprising:

a catheter formed with a fluid-delivery lumen open at the proximal end of the catheter and extending through at least a portion of the length thereof, the catheter having a distal end portion adapted to be received in a bodily orifice, an inflatable member on an exterior surface of the catheter at the distal end portion, at least one inflation aperture fluidly interconnecting the fluid-delivery lumen and the interior of the inflatable member, and at least one discharge aperture fluidly interconnecting the fluid-delivery lumen and the exterior of the catheter, the effective area of the at least one discharge aperture being smaller than the effective area of the at least one inflation aperture;

an introducer received in the fluid-delivery lumen by way of the proximal end thereof and slidably removable therefrom;

an obturator disposed within the fluid-delivery lumen intermediate the at least one discharge aperture and the at least one inflation aperture, the obturator including a plug member carried on the introducer, the plug member being substantially complementary to the interior surface of the fluid-delivery lumen, the obturator being movable between an occluded condition inhibiting flow of fluid in the fluid-delivery lumen between the at least one discharge aperture and the at least one inflation aperture during insertion of the distal end portion in the orifice and an unoccluded condition permitting flow of fluid therebetween upon removal of the introducer from the fluid-delivery lumen; and a vent provided in one of the catheter and introducer, proximally of the obturator, and fluidly interconnecting the interior of the inflatable member and the atmosphere to permit air entrapped within the inflatable member to be exhausted to the atmosphere during insertion of the distal end portion in a bodily orifice.

24. In a catheter assembly comprising a catheter having a distal end portion adapted to be received in a bodily orifice for the delivery of fluid to bodily tissue, a fluid-delivery lumen extending through at least a portion thereof and having a predetermined diameter, a fluid discharge aperture fluidly interconnected with the fluid-delivery lumen, an inflatable balloon provided on an exterior surface of the catheter at the distal end portion, and an introducer removably received in the fluid-delivery lumen, the improvement comprising:

obturator means disposed within the fluid-delivery lumen for inhibiting the flow of fluid into the inflatable balloon when the introducer is seated in the fluid-delivery lumen; and vent means provided on one of the catheter and introducer for establishing a fluid flow path between the balloon and the atmosphere when the introducer is seated in the fluid-delivery lumen.

25. A catheter assembly according to claim 18, wherein the fluid discharge aperture comprises a channel formed in the exterior surface of the catheter, one end of the channel being in fluid communication with the interior of the balloon and the other end of the channel being in fluid communication with the atmosphere, the obturator means comprising an extension of the lumen immediately adjacent to the channel and having a diameter smaller than the diameters of the fluid-delivery lumen and the introducer, the dimensions of the lumen extension, the introducer and the channel being so related that at least a portion of the lumen extension is deformed radially outwardly by the introducer to pinch the channel closed when the introducer is fully seated in the catheter fluid-delivery lumen to extend into the lumen extension.

26. In a catheter assembly comprising a catheter having a distal end portion adapted to be received in a bodily orifice for the delivery of fluid to bodily tissue, a fluid-delivery lumen extending through at least a portion thereof and having a predetermined diameter, a fluid discharge aperture fluidly interconnected with the fluid-delivery lumen and including a channel formed in the exterior surface of the catheter, an inflatable balloon provided on an exterior surface of the catheter at the distal end portion, and an introducer removably received in the fluid-delivery lumen, the improvement comprising:

obturator means for inhibiting the flow of fluid into the inflatable balloon when the introducer is seated in the fluid-delivery lumen, the obturator means including an extension of the lumen immediately adjacent to the channel and having a diameter smaller than the diameters of the fluid-delivery lumen and the introducer, the dimensions of the lumen extension, the introducer and the channel being so related that at least a portion of the lumen extension is deformed radially outward by the introducer to pinch the channel closed when the introducer is fully seated in the catheter fluid-delivery lumen to extend into the lumen extension; and vent means provided on one of the catheter and introducer for establishing a fluid flow path between the balloon and the atmosphere when the introducer is seated in the fluid-delivery lumen, wherein one end of the channel is in fluid communication with the interior of the balloon and the other end of the channel is in fluid communication with the atmosphere.

* * * * *